United States Patent [19]

Aalberse

[11] Patent Number: 4,468,470

[45] Date of Patent: Aug. 28, 1984

[54] METHOD AND A KIT FOR THE ASSAY OF ANTIBODIES TO SOLUBLE ANTIGENS

[75] Inventor: Robertus C. Aalberse, Duivendrecht, Netherlands

[73] Assignee: Stichting Centraal Laboratorium van de Bloedtransfusiedienst van het Nederlandse Rode Kruis, Amsterdam, Netherlands

[21] Appl. No.: 373,644

[22] Filed: Apr. 30, 1982

[30] Foreign Application Priority Data

May 2, 1981 [NL] Netherlands ............ 8102178

[51] Int. Cl.³ ............................................ G01N 33/54
[52] U.S. Cl. .................................... 436/539; 436/543; 436/815
[58] Field of Search ............... 436/538, 539, 540, 808, 436/543, 815; 435/7

[56] References Cited

U.S. PATENT DOCUMENTS

| | | | |
|---|---|---|---|
| 3,773,625 | 11/1973 | Sternberger et al. | 435/7 |
| 3,966,898 | 6/1976 | Sjoquist et al. | 435/7 X |
| 4,021,534 | 6/1977 | Lafontaine | 436/538 X |
| 4,228,237 | 10/1980 | Mevey et al. | 435/7 |
| 4,230,797 | 10/1980 | Boguslaski et al. | 435/7 |
| 4,232,119 | 11/1980 | Carksson et al. | 534/7 |
| 4,243,749 | 1/1981 | Sadeh et al. | 435/7 |

FOREIGN PATENT DOCUMENTS

| | | |
|---|---|---|
| 5271 | 11/1979 | European Pat. Off. |
| 2415301 | 8/1979 | France |
| 162209 | 9/1968 | Netherlands |

Primary Examiner—Arnold Turk
Attorney, Agent, or Firm—Kane, Dalsimer, Kane, Sullivan and Kurucz

[57] ABSTRACT

The invention relates to a method for the assay of antibodies to soluble antigens in an aqueous sample, in particular in body fluids, such as blood serum or blood plasma, by contacting said sample with an antigen in vitro, wherein antibodies, if present, are bound by said antigens. The invention furthermore relates to a kit for the assay and detection of antigen-specific antibodies.

According to the invention an antigen is used that is modified with a recognizable group, and said modified antigen is soluble in the test sample.

The interaction between antigen and antibody takes place in homogeneous solution.

10 Claims, No Drawings

METHOD AND A KIT FOR THE ASSAY OF ANTIBODIES TO SOLUBLE ANTIGENS

The invention relates to a method for the assay of antibodies to soluble antigens in an aqueous sample, in particular in body fluids, such as blood serum or blood plasma, by contacting said sample with an antigen in vitro, wherein antibodies, if present, are bound by said antigens. The invention furthermore relates to a kit for the assay and detection of antigen-specific antibodies in a homogeneous aqueous solution, suitable for use according to the present method.

In medical and veterinary diagnostic there is often a need for the assay of antibodies to potential pathogens in e.g. blood serum, e.g. micro-organisms, toxins, allergens, or other antigens. These antibodies are proteins with immunoglobulin (Ig) characteristics, which render them recognizable with anti-Ig reagents. Said anti-Ig reagents can be made detectable by conjugation with a radio-active isotope, an enzyme, a fluorescent dye, etc.

Such anti-Ig reagents do not differentiate between antibodies bound to a suitable antigen (i.e. antigen-antibody complexes) on the one hand and other immunoglobulins (free Ig) on the other hand. For antibody assays based upon labelled anti-Ig reagents it is therefore essential to obtain a physical separation between antigen-antibody complexes and free Ig. When the antigen in its native state is substantially larger than Ig, the antigen-antibody complex is also much larger than free Ig. An example is the assay of non-agglutinating antibodies to red cell antigens, where free and bound antibodies can be separated by centrifugation.

In the case of smaller antigens artificial enlargement of the antigen is often applied; well-established procedures are polymerization of the antigen or coupling of the antigen to an insoluble carrier. An elegant approach is the adsorption of the antigen to the inner wall of a test tube or to the surface of a plastic bead. In other procedures chemically reactive carriers are used, e.g. CNBr-activated paper discs, to which the antigen is coupled via a covalent bond.

Dutch patent specification No. 162,209 discloses a procedure of the above-mentioned type in which an antigen is used that has been bound to an insoluble carrier polymer in such a way that elution by washing does not occur. When the thus enlarged antigen is incubated with the test sample a physical separation between bound and free Ig can be easily accomplished. Free Ig can be washed away, whereas bound antibody can be detected and quantitated by means of a labelled anti-Ig reagent.

An important disadvantage of the above-mentioned procedure is, that a large number of antigen molecules concentrated on a surface are presented to the antibody-containing solution. This means that the reaction conditions are essentially different from the physiological conditions, where the antigen is in solution when it reacts with the antibody.

Another important disadvantage of the above-mentioned procedures is a practical one: when the test samples are to be tested for antibody activity towards a large number of antigens, it is obvious that a large number of solid-phase-coupled antigens have to be prepared, stored and dispensed.

The invention has in view to provide a method and a kit wherein said disadvantages are eliminated.

The method according to the invention is characterized in that an antigen is used that is modified with a recognizable group, and said modified antigen being soluble in the test sample so that an interaction between antigen and antibody occurs in a homogeneous solution, whereupon the modified antigen with the antibody bound on it, if present, is separated from the solution with a precipitating or an insoluble reagent that interacts with the recognizable group, whereas any bound antibody is then detected and/or quantitated by procedures known in the art.

According to the method of the invention instead of a solid-phase antigen a modified but soluble antigen is used, enabling the interaction between antigen and antibody in a homogeneous solution. The antigen is modified in such a way that the antigen together with bound antibody, if any, can be separated from the solution under conditions that unbound Ig remains in solution.

The modification entails the introduction of a recognizable group (H) into the antigen. The separation from the solution is accomplished with a precipitating or insoluble reagent that interacts with the recognizable group (H); this reagent will be called "anti-H".

Essential for this procedure is that the following four conditions for the reaction between H and anti-H are fulfilled:

1. The interaction between the modified antigen and the antibody should not be disrupted.
2. Free Ig does not react with anti-H.
3. Other substances in the test sample do not interfere excessively.
4. The Ig-determinants should remain available for a subsequent interaction with anti-Ig.

An important advantage of the procedure according to the invention is that the interaction between antigen and antibody takes place in homogeneous solution. Another advantage is that even if antibodies against a large number of antigens are to be tested, only one single precipitating or solid-phase reagent is required.

Good results are obtained when a hapten is used as recognizable group (H) and anti-hapten antibody coupled to a solid-phase as anti-H reagent.

Preferably as hapten trinitrophenyl is used.

Furthermore, good results are obtained when as recognizable group biotin is used and as insoluble reagent avidin, coupled to a solid-phase carrier.

As a solid-phase plastic beads are commonly used, e.g. polystyrene beads.

A microtiter plate also provides a satisfactory solid-phase.

Furthermore, chemically activated insoluble polymers can be used successfully, particularly CNBr-activated agarose beads.

The interaction between H and anti-H may depend on a covalent chemical binding, e.g. the reaction between an aldehyde group and a hydrazide group, or on non-covalent interactions, e.g. the interaction between biotin and avidine or between hapten and anti-hapten antibody.

The use of an insoluble anti-H reagent in an immunoassay is described in EPA 0 005 271 and in FR-A-2,415,301. The methods disclosed in said patent references are *competitive* immunoassays in which an *antibody* has been modified with a hapten or with biotin and in which a *labelled antigen* is used which competes with unlabelled *antigen* in the test sample. In contrast, the procedure described here is a *non-competitive* immunoassay in which an *antigen* has been modified e.g. with a hapten or with biotin and in which a *labelled anti-Ig* is used which combines with the *antibody* in the test sample.

The invention furthermore relates to a kit for the assay and determination of antibodies directed against certain antigens in a homogeneous aqueous solution suitable for use in the procedure according to the invention. This kit contains a first reagent consisting of a, with a recognizable group modified, in aqueous solution soluble antigen, a second reagent consisting of a precipitating or insoluble reagent that can interact with the recognizable group, and a third reagent consisting of a labelled anti-Ig.

According to a preferred embodiment one or more of the reagents are lyophilized.

The invention will now be illustrated with the following examples:

EXAMPLE I

In this example an experiment will be described in which IgE antibodies against an antigen in grasspollen are demonstrated; this antigen is modified by the introduction of trinitrophenyl- (TNP-)groups; the anti-H reagent consists of anti-TNP antibodies coupled to a solid-phase (plastic beads).

TNP-grasspollen was prepared by reacting 0.125 mg of trinitrobenzene sulfonic acid with 5.0 mg of dialyzed and lyophilized grasspollen extract in 0.2M sodium borate buffer pH 9.0 in a final volume of 0.85 ml.

After a reaction time of 2 hrs at 20°-24° C. and 16 hrs at 0°-4° C. the solution was dialyzed against phosphate-buffered saline (PBS).

Anti-TNP antiserum was raised by immunizing a sheep with TNP-substituted bovine serum albumin according to standard procedures. From this antiserum the antibodies were isolated by adsorption onto TNP-Sepharose according to procedures known in the art; the adsorbed antibodies were eluted by a buffer consisting of 0.1M glycine, 0.15M NaCl and 10% (w/v) dioxane, pH 2.5. The eluted antibodies were transferred into PBS by gelfiltration over Sephadex G25.

The optical density at 280 nm of the solution obtained was 0.400. These anti-TNP antibodies were adsorbed onto polystyrene beads ($\phi\frac{1}{4}''$) by 16 hrs incubation at 20°-24° C. in a 1:20 dilution of the antibody-containing solution in 0.1M NaHCO$_3$ buffer pH 9.0.

For the assay of antibodies of the IgE class against grasspollen, 50 µl serum from a hayfever patient P. or from a control donor C, was added to 200 µl of a solution of TNP-grasspollen diluted 1:4000 in PBS containing 0.5% BSA and 0.02% Tween-20, and subsequently incubated for 6 hrs at 20°-24° C.

The polystyrene bead coated with anti-TNP antibodies was washed in order to remove the non-adsorbed anti-TNP antibodies and then transferred to the reaction mixture of serum and TNP-pollen extract. After 16 hrs incubation at 20°-24° C. non-bound material was removed by washing the beads; bound-IgE antibodies to grasspollen were detected and quantitated with a $^{125}$I-labelled anti-IgE reagent.

| Hayfever patient P, dilutions | % binding of labelled anti-Ig reagent |
| --- | --- |
| 50 µl - | 50.2 |
| 50 µl - 1:25 | 35.5 |
| 50 µl - 1:50 | 27.8 |
| 50 µl - 1:100 | 17.5 |
| 50 µl - 1:200 | 11.6 |
| 50 µl - 1:400 | 7.6 |
| 50 µl - 1:800 | 4.6 |
| 50 µl - 1:1600 | 3.1 |
| 50 µl - 1:3200 | 2.5 |
| 50 µl - 1:6400 | 1.9 |
| 50 µl - 1:12,800 | 1.5 |
| 50 µl control donor | 1.0 |

EXAMPLE II

The glycoprotein avidin has a high affinity ($K=10^{-15} M^{-1}$) for biotin. Binding of avidin to a solid-phase and coupling biotin to an antigen enables the separation between antigen-bound immunoglobulin and free immunoglobulin.

Avidin was coupled covalently to CNBr-activated Sepharose-4B according to standard procedures; 3.5 mg of avidin was coupled to 1 ml of Sepharose; the reaction product was suspended in 350 ml of PBS.

Biotin-grasspollen was prepared by reacting 1 mg grasspollen in 0.5 ml of PBS with 240 µg of biotin-succinimide in 20 µl of dimethyl formamide for 4 hrs at 20°-24° C.

Uncoupled and inactivated biotin-succinimide was removed by dialysis against PBS for 16 hrs.

For the assay of antibodies of the IgE class against grasspollen, 50 µl of serum from a hayfever patient P or from a control donor C, was added to 50 µl of a solution of biotin-grasspollen diluted 1:100 in PBS containing 0.5% of BSA and 0.02% of Tween-20, and subsequently incubated for 1 hr at 20°-24° C. Next, 0.5 ml of avidin-Sepharose suspension was added and 250 µl of PBS that contained bovine serum albumin and sodium EDTA. The mixture was incubated for 16-24 hrs on a rotator.

The Sepharose-protein complex was separated from the suspension by centrifugation. Non-bound Ig was removed by washing the Sepharose beads with a 0.9% saline solution.

Quantitation of bound IgE was accomplished by addition of $^{125}$I-labelled anti-IgE antibodies to the suspension of the Sepharose-protein complex.

| Hayfever patient P, dilutions | % binding of labelled anti-Ig reagent |
| --- | --- |
| 50 µl - 1:25 | 32.7 |
| 50 µl - 1:50 | 20.6 |
| 50 µl - 1:100 | 15.1 |
| 50 µl - 1:250 | 6.4 |
| 50 µl - 1:500 | 4.9 |
| 50 µl - control donor | 0.5 |

I claim:

1. In a method for the assay of antibodies to soluble antigens in an aqueous sample, by contacting said sample with antigens in vitro, wherein antibodies, if present, are bound by said antigens, the improvement which comprises utilizing an antigen that is modified with a recognizable group, said modified antigen being soluble in the test sample so that an interaction between antigen and antibody occurs in a homogeneous solution, and reacting the modified antigen with the antibody bound to it, if present, with a precipitating or an insoluble reagent that interacts with the recognizable group, wherein said bound antibody is separated from the sample solution while unbound antibody remains in solution, and analyzing said bound separated antibody.

2. The method according to claim 1, characterized in that hapten is used as recognizable group and anti-hapten antibody coupled to a solid-phase as insoluble reagent.

3. The method according to claim 2, characterized in that as hapten, trinitrophenyl is used.

4. The method according to claim 1, characterized in that as recognizable group biotin is used and as insoluble reagent avidin, coupled to a solid-phase carrier.

5. The method according to claims 2, 3, or 4, characterized in that as a solid-phase plastic beads are used.

6. The method according to claims 2, 3, or 4, characterized in that as a solid-phase carrier a microtiter plate is used 7. The method according to claim 2 characterized in that as solid-phase carrier chemically activated insoluble polymers are used.

8. The method according to claim 7, characterized in that as insoluble polymers CNBr-activated agarose beads are used.

9. A kit for the assay and determination of antibodies directed against certain antigens in a homogeneous aqueous solution characterized in that said kit contains a first reagent consisting of an aqueous solution including a soluble antigen that is modified with a recognizable group, said modified antigen being reactable with the antibodies to be determined, a second reagent consisting of a precipitating or insoluble reagent that can interact with the recognizable group, and a third reagent consisting of labelled anti-Ig combinable with antibodies to be determined.

10. The kit according to claim 9, characterized in that one or more of the reagents are lyophilized.

* * * * *